United States Patent [19]

Wied et al.

[11] 4,129,381
[45] Dec. 12, 1978

[54] APPARATUS AND METHOD FOR PREPARING A PARTICLE SUSPENSION

[75] Inventors: George L. Wied, Chicago, Ill.; Gunter F. Bahr, Washington, D.C.; James H. Puls, Chicago, Ill.

[73] Assignee: Miles Laboratories, Inc., Elkhart, Ind.

[21] Appl. No.: 736,516

[22] Filed: Oct. 28, 1976

[51] Int. Cl.² .................. G01N 1/00; G01N 21/00
[52] U.S. Cl. ................................. 356/36; 137/93; 250/575; 356/73
[58] Field of Search ............... 356/36, 73, 103, 181; 137/3, 93; 250/575

[56] References Cited

U.S. PATENT DOCUMENTS

| | | | |
|---|---|---|---|
| 2,044,164 | 6/1936 | Gulliksen | 137/93 |
| 3,019,091 | 1/1962 | Schneider, Jr. | 356/181 |
| 3,088,479 | 5/1963 | Christie | 356/181 |
| 3,498,719 | 3/1970 | Wing et al. | 356/181 |
| 3,827,805 | 8/1974 | Mansfield et al. | 356/73 |
| 3,968,006 | 7/1976 | Zimmerman | 356/181 |
| 3,987,808 | 10/1976 | Carbonell et al. | 137/3 |
| 4,017,190 | 4/1977 | Fischel | 356/181 |

*Primary Examiner*—Vincent P. McGraw
*Attorney, Agent, or Firm*—Roger N. Coe

[57] ABSTRACT

Apparatus and a method for preparing a particle suspension by measuring and adjusting the concentration of a suspension while the suspension is being subjected to particle-dispersing physical agitation are disclosed. The invention has particular application to the preparation of a cytologic specimen exhibiting isolated single cells, which specimen can be subjected to machine analysis in a flowthrough type counter or be applied to slides with even dispersion and uniform density in monocellular layers suitable for microscopic analysis.

9 Claims, 4 Drawing Figures

APPARATUS AND METHOD FOR PREPARING A PARTICLE SUSPENSION

FIELD OF THE INVENTION

The present invention relates to preparation of a particle suspension and, more particularly, to measuring and adjusting the concentration of the suspension simultaneously with the physical dispersion of the particles.

BACKGROUND OF THE INVENTION

The microscopic screening of cytologic samples is a tedious, time-consuming, repetitious task that technicians are often required to perform a hundred or more times every working day.

All tissues are composed of cells, the cell being the basic living unit of animal and plant matter. Many body organs are composed of or lined by epithelial tissue. As a result of continuous growth and replacement the most superficial cells of an epithelium are constantly shed and replaced by younger cells in a form of spontaneous exfoliation. Exfoliated cells are found in body fluids such as secretions from the female genital tract, gastric fluid, urine, cerebrospinal fluids, punctates exprimates or washings from epithelial surfaces. These exfoliated cells can be collected from certain body sites for microscopic examination. In addition, spontaneously exfoliated cells can be supplemented by cells obtained directly from certain organs by use of suitable instruments. Such cells can be employed for detection and diagnosis of various pathological conditions.

Automation of this task would speed up the identification of abnormal cells, eliminate the problem of human fatigue associated with microscopic analysis and tend to reduce the overall cost of such analysis. Identification of single abnormal cells is at the core of any successful automation procedure. In order to achieve this goal it is necessary to prepare isolated single cells for flow-through type counters or a specimen approximating a cell monolayer for microscopic analysis. Techniques already exist for the identification of the complete spectrum of gynecologic cells in a clean specimen of isolated cells. However, techniques do not exist at the present for the adequate preparation of a specimen which constitutes a suspension of isolated single cells without cell overlap, cell aggregation, cell loss, or cell damage. Overlapping cell nuclei, groups of closely-packed polymorphonuclear leucocytes, and dark cytoplasmic areas are frequently incorrectly interpreted by automatic or semi-automatic machine screening as large, dark "malignant" nuclei. Once a proper suspension has been achieved, problems specific to automated flow-through systems or for automated slide base systems are within the capabilities of present technology.

The detection of carcinoma in the female genital tract is a prime example of the use of diagnostic cytology or human cell interpretation. Exfoliated cells which accumulate in the vagina together with cells scraped from the uterine cervix provide the cytopathologist with information for detecting carcinoma with a high rate of reliability. Cytologic material presently collected from the vagina or uterine cervix and/or uterine cavity by a physician or trained paramedic personnel is smeared on glass slides and fixed to preserve morphologic and chemical structure. Samples are sent to the cytology laboratory in which they undergo an elaborate staining procedure, such as Papanicolaou stain. After staining, the slides are scanned under a microscope by cytotechnicians trained to identify normal and abnormal cells. Since the great majority of smears can be expected to be normal, it is apparent that some sort of automatic apparatus would be of significant value in screening out all obviously normal smears, leaving questionable and abnormal ones for further examination by cytotechnicians and pathologists.

Various automatic apparatus have been built to monitor cells based chiefly on differences in cell area or size along with total cell radiation, absorption or cell optical density. The reliability of such apparatus has proved to be extremely poor when separating the spectrum of cells under consideration.

The single most significant problem in preparing specimens has been the clumping of cells which makes it impossible for a machine to discriminate between the signal originating, for example, from a single cancer cell and the signal resulting from a cluster of benign cells which electronically could have similar parameters. This problem has not been obviated by the various attempts at automation which have been introduced in recent years, including agitation, homogenation, syringing, force filtration, ultrasonics, shaking, stirring, and the like to achieve dispersal of cell aggregates. Such cell aggregates, often composed of only two or three cells, have persisted as the major obstacle to full automation, since they can be particularly misleading to automated equipment. In contrast, the human counterpart has little difficulty in supressing extraneous visual information and cytologists can read slides containing tissue fragments, overlapping cells, and the like.

The difficulty with efforts to artificially or chemically disrupt cells has been the extensive damage which normally occurs during such attempts. Some mechanical methods, for example, tear cells apart and can also rip away parts of cell membranes and cytoplasm. The insuing cellular damage can make the specimen unacceptable for automatic analysis, since the cells are destroyed and automated equipment cannot contend with the resulting debris. Ultrasonic dispersion in particular tends to be too violent to be used as a method for cell dispersal. It frequently results in extensive cell damage, with the production of cytoplasmic fragments. Treatment with a homogenizer, such a household or laboratory blender, e.g., a Waring blender, produces an especially violent result, tending to cause extensive cell damage and destruction.

Syringing is one of the simplest methods of dispersing cells, but syringing has to be performed very carefully in order to achieve the desired result. Little success has been achieved with forced filtration. Apparently, the shearing forces are of insufficient strength and are applied for insufficient time to break down the cellular attachments. Rapid shaking, as with a Vortex mixer, readily disperses cell clumps, but has little or no effect on tissue fragments.

Attempts have also been made to chemically separate cell clusters. Analysis of the cell junction in cervical samples tends to suggest that desmones bind endocervical normal and malignant cells in situ. Desmones are ubiquitous cell juntions. It is extremely difficult to separate cells by disrupting desmones without destruction of the cell membrane. Consequently, most chemical approaches have failed because attacks on the cell juntion also resulted in destroying the cell membranes themselves.

SUMMARY OF THE INVENTION

An object of the present invention is to provide apparatus and a method for measuring and adjusting the concentration of a suspension while the suspension is subjected to physical agitation.

Another object of the present invention is to provide apparatus and a method for preparing a cell suspension of a cytologic specimen, which suspension can be applied to slides in substantially monocellular layers.

Still another object of the present invention is to provide apparatus and a method for suspending isolated single cells without cell overlap, cell loss or cell damage.

A further object of the present invention is to provide apparatus and a method for simultaneously diluting a suspension of particles while breaking up particle clumps.

Yet another object of the present invention is the preparation of a particle suspension which can be subjected to accurate machine analysis.

In accordance with the present invention the suspension and dispersion of particles occur inside a receptacle or vessel. The suspension is continually agitated while dilution of the suspension is being measured and regulated. Light is passed through the suspension and measured by light sensing means which detect scattered and direct light. The resulting measurement is monitored to compare the concentration of the suspension to a predtermined concentration and to control the addition of diluent to the suspension. In a preferred embodiment, disposable syringes are used for both dispersion and dilution of cytologic samples.

BRIEF DESCRIPTION OF THE DRAWINGS

Other and further objects, advantages and features of the invention will be apparent to those skilled in the art from the following detailed description thereof, taken in conjunction with the accompanying drawings in which.

DESCRIPTION OF THE PREFERRED EMBODIMENTS

Figure 1:
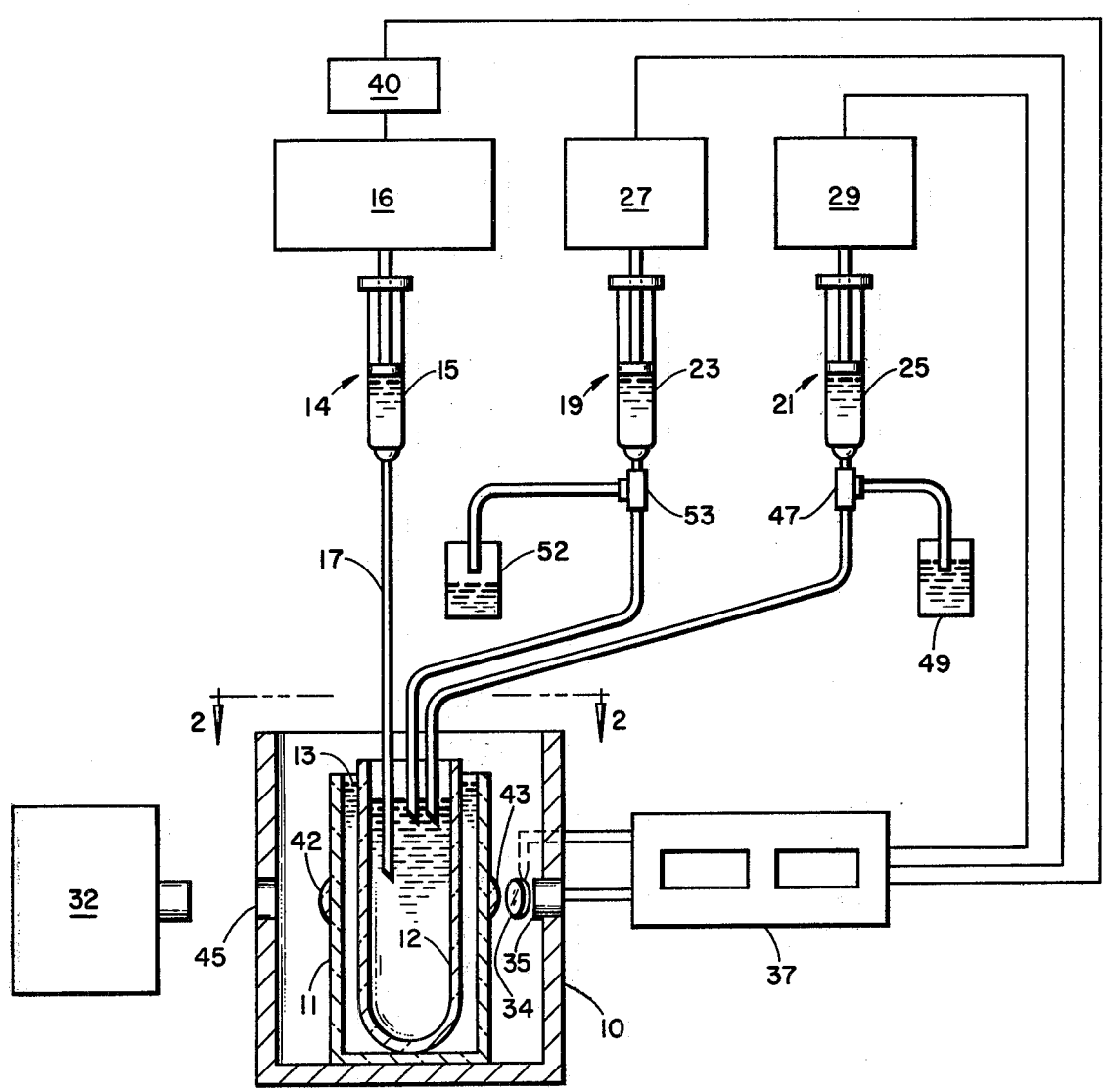
FIG. 1 is a diagrammatic view, partly in cross section, of apparatus in accordance with the present invention.

Apparatus used in the present invention for monitoring and adjusting the concentration of a suspension of particles while an active process of dispersing the particles is underway is illustrated in FIG. 1 of the drawings. The apparatus comprises a chamber 10 which contains a light transmitting receptacle or vessel 12 for accommodating a sample suspension of particles, for example a cell suspension from which a cytological specimen is to be prepared. Dispersing unit 14 is a piston type pump 15 having an elongated tube means 17 of restricted bore connected thereto and extending into the vessel 12 as shown. Pump 15 and tube means 17 can take the form of a disposable hypodermic syringe and cooperable needle as shown. The piston of pump 15 is driven by a reciprocating actuator means 16, and operates to repeatedly pump the suspension alternately in opposite directions through tube means 17.

Excess fluid is removed from vessel 12 by withdrawal unit 19 comprising pump 23. Dilution of the suspension is regulated by dilution control unit 21 which can comprise pump 25 for supplying diluent to vessel 12 as required to achieve a desired dilution. The pistons or plungers of pumps 23 and 25 are reciprocatably driven, respectively, by actuators or motors 27 and 29. Pumps 23 and 25 can take the form of disposable hypodermic syringes.

In operation, illumination is provided by a light source 32. Light passing through the suspension in vessel 12 is measured by light sensing means which may take the form of photoelectric cells 34 and 35 which are positioned to detect scattered and direct light, respectively. The signals generated by photoelectric cells 34 and 35 are monitored in monitoring unit 37 which compares the signals with predetermined standards. As explained in more detail hereinafter, a feedback circuit is connected to motors 27 and 29 for regulating the withdrawal or addition of fluid.

This invention has particular application to the preparation of a cytological specimen of substantially uniform density which can be analyzed by a machine. The apparatus and method of the invention are accordingly described in the following portion in the context of measuring and adjusting the concentration of a suspension of body tissue cells. However, it will be understood that in its broadest application the invention can be used with respect to any suspension, including the dispersion of pigments in the paint industry, the dilution of ink pigments, the dispersion of dye for the textile industry, the dilution of polystyrene latex spheres and the like in these applications in which there is a need for measuring and automatically adjusting the concentration of the suspension.

Figure 2:
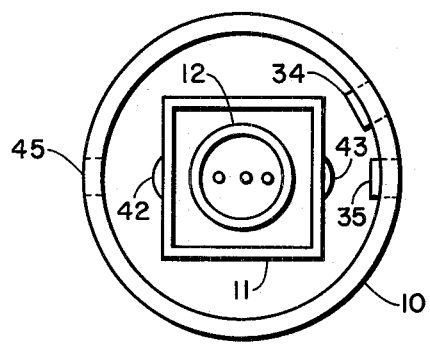
FIG. 2 is a top plan view, along lines 2—2 in FIG. 1.

Referring to FIGS. 1 and 2, pump 15 is capable of dispersing cells in a sample, such as that obtained from a standard PAP smear. For purposes of obtaining the sample, conventional specimen collection procedures can be employed, including a scrape, aspiration, swab and others. Conventional wooden spatulas, however, should be avoided for collecting specimens intended for automated analysis, since use thereof cause the specimen to be seeded with wooden particles. Plastic spatulas, scrubbed to remove loose bits of plastic, can be substituted for wooden spatulas. Advantageously, the specimen, such as a cervical scrape specimen, is suspended in a fluid such as a balanced salt solution which provides good cell preservation and little or not interference with subsequent staining. Normal saline alone can be used as a collecting liquid if the specimen is processed promptly. Another collecting liquid has the following composition:

| | |
|---|---|
| NaCl | 8.00 grams |
| KCl | 0.20 grams |
| $NaH_2PO_4H_2O$ | 0.005 grams |
| $NaHCO_3$ | 1.00 grams |
| $KH_2PO_3$ | 0.2 grams |
| $H_2O$ | 1000 milliliters |

Virtually all routine cervical scrape samples contain some cell aggregates. The mean percentage of cells in the form of aggregates has been determined as approximately 47.4%. The purpose of pump 15 and tube means 17 is that of a deagglomeration unit which will break down cell clumps without destroying the cells involved. Typically, pump 15 is either a five cubic centimeter or a ten cubic centimeter disposable hypodermic syringe having a 19, 20 or 21 gauge (S.W.G.) needle forming tube means 17. The piston of pump 15 can be reciprocated by actuator means 16 which may include an electrically driven motor; such piston action being effective to repeatedly pump suspension to and from vessel 12 through tube means 17. This repeated pumping action is believed to cause cells or particles to disperse through the shearing process which occurs. Reciprocal activating device model 681 supplied by Harvard Apparatus of Millis, Mass. has been found to be suitable for use as the actuator means 16 for the piston of pump 15. With an actuator of this type both the stroke and rate of piston movement are variable over a fairly wide range. Control means 40 for actuator means 16 provides adjustment of the speed and duration of the pumping operation. For example, control means 40 can be a simple timer and/or rheostat. Alternatively, a digital controlled stepping motor can be used to serve the dual function of actuator means 16 and control means 40. The number of steps can be regulated to control movement since such motors move incrementally one step for each pulse. A 200 step motor, for example, moves 1.8° for each pulse. By controlling the speed of the pulses one can control how fast the motor turns. Such a stepping motor would, of course, be equipped with a mechanical converter to convert rotary motion into reciprocal motion.

While 19, 20 or 21 gauge tubes for tube means 17 are preferred, it will be understood that other sizes such as tube means or needles of 18 or 23 gauge can be employed. What is important is that the amount of fluid passing through tube means 17 within a given period of time and the size of tube means 17 be such as will not cause damage to the cells while effecting the desired deagglomeration.

Many of the techniques previously used for dispersion of cells were found to be effective in dispersing cells grown in tissue culture, but were not effective when applied to clinical gynecologic material. Of course, the major diagnostic interest lies in the analysis of samples of normal, atypical, dysplastic and malignant cells.

Chamber 10, in which the suspension and dilution of cells occurs, is preferably painted a dull black inside to minimize extraneous light reflections and is large enough to hold container 11. Chamber 10 can be regulated to control the temperature of the suspension inside vessel 12. The use of heating or cooling coils (not shown) is one way in which the temperature of chamber 10 can be regulated.

Container 11 can be a cuvette which is adapted to house vessel 12, e.g., a sample tube or vial containing the suspension of cells in a predetermined amount (e.g., 5 milliliters) of an initial dispersing solution. If desired, the sample present in the initial dispersing solution can be gently mixed using a Vortex mixer before inserting the sample tube or vial into test chamber 10. In order to reduce light scattering the space between container 11 and vessel 12 is filled with fluid 13, such as mineral or paraffin oil of approximately the same refractive index as that of Pyrex ® glass. Advantageously, container 11 can have lenses present, such as plano-cylindrical lenses 42 and 43, which disperse and collect light passing through the suspension in vessel 12. These lenses are preferably applied with optical cement onto container 11, but could be held in position mechanically.

Figure 3:
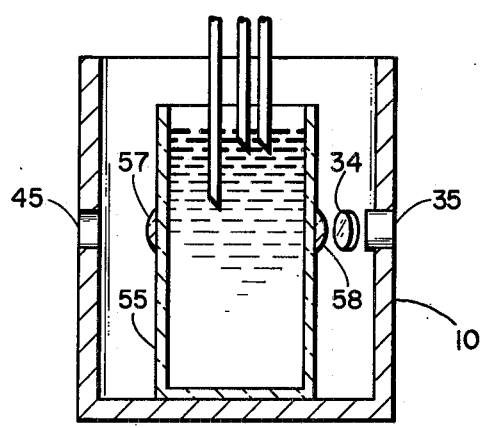
FIG. 3 is a diagrammatic view, partly in cross section of a modified form of receptacle or vessel which is useful in the present invention.

If desired, a single plastic or glass container, with or without lenses affixed, can be substituted for the combination of container 11 and vessel 12, thereby eliminating the necessity for the use of multiple containers and the presence of fluid between the containers in order to minimize refractance. Such an embodiment is shown in FIG. 3 in which a single vessel 55 is present inside chamber 10. Lenses 57 and 58 can be affixed to vessel 55.

Illumination is provided from light source 32, which can be a coherent or incoherent light source. A preferred light source is a laser such as helium-neon laser number 79050 sold by Edmund Scientific Company in Barrington, N.J. That laser provides a light source of approximately 6,000 Angstroms. The source of illumination in the form of a laser beam is desirable since it requires no special shaping, it is very narrow and therefore is eminently suitable for making measurements. However, the apparatus is not limited to the use of a thin ribbon of light and in some applications it will undoubtedly be found desirable to utilize a beam of light having a thicker cross section.

Light passes through opening 45 in chamber 10, through the suspension in vessel 12 of FIGS. 1 and 2 or vessel 55 of FIG. 3 and is then measured by light sensing means such as photoelectric cells 34 and 35 located on the opposite side of chamber 10 from light source 32. Preferred photoelectric cells are sold by E. G. and G. of Salem, Mass. as part No. HAV1000A. Photocell 35 is responsive to direct light, while photocell 34 is responsive to scattered light. These photocells, located at an angle of approximately 15° to each other, are connected to control a monitoring unit 37 which amplifies the signals obtained from the photocells and preferably provides a visual indication of the existing concentration of the suspension of cells in vessel 12. A suitable monitoring unit could comprise a SBC 80/10 microprocessor, sold by Intel of Santa Clara, Calif. with suitable interfaces to 27, 29, 34, 35 and 40 and a power supply. For convenience in monitoring the signals digital meters such as those sold by Andlogic of Wakefield, Mass. as part number 2533LP can be used.

Maximum transmission of light through vessel 12 occurs when there is no suspension present. Hence scattering is at a minimum in the absence of suspension and increases with increasing concentration. Monitoring unit 37, which can be a logic sequencer or a microprocessor, can be preset to a desired concentration and thereby programmed to terminate the sequence of operation when a desired concentration has been achieved. Signals from monitoring unit 37 are used to control motor 29 and motor 27, and thereby effect the addition of diluent to vessel 12 or the removal of excess diluent material from vessel 12, and control the operation of control means 40.

More specifically, motor 29, which is, for example, a digital stepping motor, is used to depress a plunger on dilution pump 25, which may be a disposable tuberculin syringe. Pump 25 can be connected by means of a three way valve 47 to a reservoir or diluent supply tank 49 containing a suitable diluent which is not detrimental to cells in suspension. One suitable solution is Hank's BSS solution made up without calcium, magnesium or phenol red dye. Thus, upon activation of motor 29 the piston in pump 25 is pushed downwardly and diluent from reservoir 49 is pumped into vessel 12 until a correct concentration of the suspended cells has been achieved.

To prevent sample overflow it is at times necessary to remove suspension from vessel 12. This is achieved by activating motor 27, which can be digital stepping motor, and causing the plunger in pump 23 to be drawn upwardly thereby simultaneously withdrawing suspension from vessel 12. Regulation of motor 27 by monitoring unit 37 is easily controlled since the amount of fluid which must be withdrawn and the timing for such withdrawal can be determined based on the amount of fluid in vessel 12 initially and the amount of fluid added by pump 25. When the sum of the fluid initially present in vessel 12 plus that added via pump 25 exceeds a predetermined amount motor 27 can be activated to withdraw excess fluid. The design of the unit for withdrawal of fluid can accordingly be very similar to the unit designed for diluting the fluid suspension in vessel 12. A separate chamber or overflow tank 52 can be connected by means of a three-way valve 53 for the purpose of storing any fluid withdrawn from vessel 12.

Figure 4:
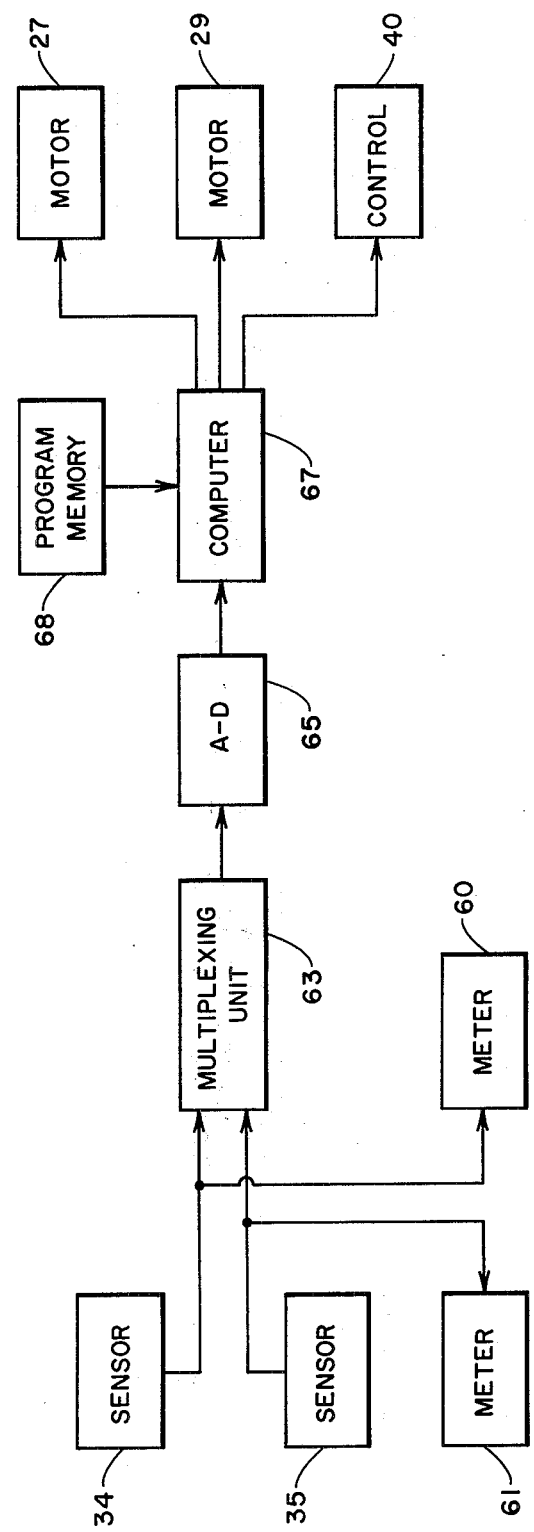
FIG. 4 is a block diagram of a control system which is useful in the present invention.

A block diagram of a control system which can be used in the present invention is illustrated in FIG. 4. Light sensing means or sensors, such as photoelectric cells 34 and 35, measure the light passing through the suspension of particles. If desired, the signals obtained from said photoelectric cells can be displayed on meters 60 and 61, respectively. For example, meters 60 and 61 can be digital display meters. The signals from the sensors or photoelectric cells 34 and 35 are passed through a multiplexing unit 63 to an analog-digital (A-D) converter 65 and then to computer 67 controlled by memory 68. In computer 67 the signals from analog-digital convertor 65 are compared to predetermined values for a desired particle suspension. The signal from sensor cell 34 is used to control dispersion by regulating control means 40 and the signal from sensor cell 35 is used to control dilution by regulating pump 29. Until the desired particle suspension is achieved and said predetermined values reached power is supplied to control means 40 and to motor 29 to simultaneously bring about deagglomeration and dilution. If dilution approaches the maximum capacity of the dilution chamber or vessel, power is supplied to motor 27 for a given period of time causing the withdrawal of fluid from the dilution vessel. Once the predetermined dilution has been achieved both dilution and agitation are stopped by computer 67.

The vessel containing the diluted sample can then be removed from the apparatus and the diluted sample can be introduced into automatic counting equipment, applied to slides for analysis of the diluted particles, or otherwise treated in accordance with known procedures. One procedure, for example, is simply to drop the suspension of particles onto a slide. Another approach is to pour the diluted sample into a slide centrifuge and permit liquid containing particles to escape onto a slide during a centrifuging operation. It will be understood, however, that the manner of using the diluted samples does not form part of the present invention.

It will be seen that the design of the system is such that the only apparatus which comes in contact with the suspension of cells can be disposable equipment. This is particularly important to prevent contamination between a sample containing cancer cells and a normal sample. It will also be seen that only three needles or tubes are required to be fitted into vessel 12. This is important because of the space limitations of the system and because it facilitates working with very small specimen volumes. It will be understood that for convenience the respective tube means connecting units 14, 19 and 21 have been shown in FIG. 2 lined up in a straight line in vessel 12. The tube means need not be so aligned and may, if desired, be extended to any depth in vessel 12.

From the foregoing it will be seen that this invention is well adapted to attain all of the ends and objects herein above set forth together with other advantages which are obvious and which are inherent to the system. The apparatus of the present invention has the advantages of convenience, simplicity, relative inexpensiveness, effectiveness, durability, accuracy and directness of action. The invention substantially overcomes the problem of achieving a monolayer suspension of biological cells necessary for the preparation of evenly dispersed slides of uniform density suitable for machine analysis. A small vial containing specimen can be shipped to a testing center for analysis, where proper dilution occurs to approximately 30,000 cells per milliliter. Cell clumps are deaggregated by the pumping action to and fro through a pump such as a hypodermic syringe needle. The system has a further advantage of not requiring the use of a reference light. Once a known concentration has been prepared, standard methods can be used to prepare a specimen for machine analysis. The resulting diluted samples are virtually free from the dense clumps of overlapping squamous and endocervical cells that frequently occur in slides prepared by conventional smear techniques. In addition, the cells are well preserved with little sign of any damage. Slides using diluted specimens prepared according to this invention are far more suitable for automatic analysis than direct smears because of the more even distribution of cells. The diluted specimens can be applied to slides by any conventional techniques, including centrifugal force.

While light scattering is a known approach to the measurement of particle concentration it has not been possible to constantly monitor the concentration of suspension while simultaneously actively dispersing particles, particularly biological specimens, in such a manner as to deagglomerate cells without cell loss or cell destruction.

Although the use of pump 15 and tube means 17 are preferred means for breaking up clumps of particles, such as cells, it will be understood that other means, such as ultrasonic probes, can be used when the nature of the suspended particle is such that the particles will not be destroyed or damaged by the utilization of more violent forms of agitation.

As indicated herein the method of the present invention is capable of being regulated automatically. It will be understood, however, that if desired, operation of the pumps and/or regulation of the speed of the pumps can be made manually.

As previously indicated, the present invention has many practical applications. The system can be used, for example, to insure optimum dilution of a sample, to monitor liquids in waste treatment plants, for controlling consistency of food products, for monitoring stack gases for particulate matter, for regulating pigment concentration in paints, inks and dyes, for achieving a desired suspension of cement particles, and for providing optimum dilution of a sample prepared for gel electrophoresis columns.

Obviously, many other modifications and variations of the invention as herein before set forth can be made without departing from the spirit and scope thereof.

What is claimed is:

1. Apparatus for measuring and adjusting the concentration of a fluid suspension of cells while said suspension is subjected to particle-dispersing physical agitation, which comprises:
   a light transmitting receptacle for retaining a suspension of cells;
   agitation means for subjecting a suspension of cells in said receptacle to physical agitation to break up cell clumps without destroying the cells;
   diluting means for diluting a suspension of cells in said receptacle to achieve a desired particle concentration;
   a light source for passing a light beam through said receptacle;
   first light sensing means positioned to receive direct light from said source passed through said receptacle and obtain a first light signal;
   second light sensing means positioned to receive scattered light from said source passed through said receptacle and obtain a second light signal;
   monitoring means connected to said first light sensing means and to said diluting means for comparing the first light signal with a predetermined value for dilution and for regulating the diluting means in response thereto to achieve the desired concentration of cells in suspension in said receptacle; and
   monitoring means connected to said second light sensing means and to said agitation means for comparing the second light signal with a predetermined value for dispersion and for regulating the agitation means in response thereto to achieve the desired dispersion of cells in suspension in said receptacle.

2. Apparatus of claim 1 further including withdrawing means for removing excess fluid from the receptacle.

3. Apparatus of claim 2 in which the agitation means, diluting means and withdrawing means each constitute a piston operated device.

4. Apparatus of claim 1 in which the first and second light sensing means are each photoelectric cells located at an angle of approximately 15 degrees to each other.

5. Apparatus of claim 1 which further includes lenses located on opposite sides of the receptacle for respectively dispersing and collecting light as it passes through said receptacle.

6. The method for measuring and adjusting the concentration of a fluid suspension of cells while said suspension is subjected to particle-dispersing physical agitation, which method comprises:
   placing a fluid suspension of cells inside a light transmitting receptacle;
   subjecting the fluid suspension in said receptacle to physical agitation to break up cell clumps without destroying the cells;
   passing a light beam through the fluid suspension in said receptacle;
   measuring the direct light transmitted through the receptacle;
   measuring the scattered light transmitted through the receptacle.
   comparing said direct light with a first predetermined light value;
   comparing said scattered light with a second predetermined light value;
   terminating the dilution of the fluid suspension in said receptacle when the direct light is substantially identical with said first predetermined light value; and
   terminating the agitation of the fluid suspension in said receptacle when the scattered light is substantially identical with said second predetermined light value.

7. Apparatus for measuring and adjusting the concentration of a particle suspension while said suspension is subjected to particle-dispersing physical agitation, which comprises:
   a light transmitting receptacle for retaining a suspension of particles;
   agitation means for subjecting a suspension of particles in said receptacle to physical agitation; diluting means for diluting a suspension of particles in said receptacle to achieve a desired particle concentration;
   a light source for passing a light beam through said receptacle;
   first light sensing means positioned to receive direct light from said source passed through said receptacle and obtain a first light signal;
   second light sensing means positioned to receive scattered light from said source passed through said receptacle and obtain a second light signal;
   monitoring means connected to said first light sensing means and to said diluting means for comparing the first light signal with a predetermined value for dilution and for regulating the diluting means in response thereto to achieve the desired concentration of particles in suspension in said receptacle; and
   monitoring means connected to said second light sensing means and to said agitation means for comparing the second light signal with a predetermined value for dispersion and for regulating the agitation means in response thereto to achieve the desired dispersion of particles in suspension in said receptacle.

8. Apparatus as in claim 7 in which the agitation means comprises elongated restricted bore tube means and pump means for pumping suspension alternately in opposite directions through said tube means.

9. The method for measuring and adjusting the concentration of a suspension of particles while said suspension is subjected to particle-dispersing physical agitation, which method comprises:
   placing a fluid suspension of particles inside a light transmitting receptacle;
   subjecting the fluid suspension in said receptacle to physical agitation;
   passing a light beam through the fluid suspension in said receptacle;
   measuring the direct light transmitted through the receptacle;
   measuring the scattered light transmitted through the receptacle;
   comparing said direct light with a first predetermined light value;
   comparing said scattered light with a second predetermined light value;
   terminating the dilution of the fluid suspension in said receptacle when the direct light is substantially identical with said first predetermined light value; and terminating the agitation of the fluid suspension in said receptacle when the scattered light is substantially identical with said second predetermined light value.